(12) United States Patent
Walters et al.

(10) Patent No.: US 8,343,902 B2
(45) Date of Patent: *Jan. 1, 2013

(54) LOW-IRRITATING, CLEAR CLEANSING COMPOSITIONS WITH RELATIVELY LOW PH

(75) Inventors: Russel M. Walters, Philadelphia, PA (US); Euen T. Gunn, Trenton, NJ (US); Lisa Gandolfi, Franklin Park, NJ (US); Donzel Johnson, Morrisville, PA (US); Emmanuel Anim-Danso, Ewing, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/822,329

(22) Filed: Jun. 24, 2010

(65) Prior Publication Data

US 2011/0319306 A1    Dec. 29, 2011

(51) Int. Cl.
*A61K 7/06* (2006.01)

(52) U.S. Cl. ........ 510/130; 510/424; 510/426; 510/428; 510/475

(58) Field of Classification Search .................. None
See application file for complete search history.

(56) References Cited

U.S. PATENT DOCUMENTS

| | | | |
|---|---|---|---|
| 2,129,264 A | 9/1938 | Downing et al. | |
| 2,178,353 A | 10/1939 | Werntz | |
| 2,774,786 A | 12/1956 | Erickson | |
| 2,813,898 A | 11/1957 | Gaertner | |
| 2,828,332 A | 3/1958 | Gaertner | |
| 3,318,817 A | 5/1967 | Smith | |
| 3,950,260 A | 4/1976 | Eldib | |
| 4,110,263 A | 8/1978 | Lindemann et al. | |
| 4,186,113 A | 1/1980 | Verdicchio et al. | |
| 4,215,064 A | 7/1980 | Lindemann et al. | |
| 4,233,192 A | 11/1980 | Lindemann et al. | |
| 4,372,869 A | 2/1983 | Lindemann et al. | |
| 4,380,637 A | 4/1983 | Lindemann et al. | |
| 4,382,036 A | 5/1983 | Lindemann et al. | |
| 4,443,362 A | 4/1984 | Guth et al. | |
| 4,552,685 A | 11/1985 | Kernstock et al. | |
| 4,617,414 A | 10/1986 | Lukenbach et al. | |
| 4,726,915 A | 2/1988 | Verdicchio | |
| 5,004,557 A * | 4/1991 | Nagarajan et al. ............ 510/337 |
| 5,130,056 A | 7/1992 | Jakobson et al. | |
| 5,215,976 A | 6/1993 | Fost et al. | |
| 5,286,719 A | 2/1994 | Fost et al. | |
| 5,478,490 A | 12/1995 | Russo et al. | |
| 5,648,348 A | 7/1997 | Fost et al. | |
| 5,650,402 A | 7/1997 | Fost et al. | |
| 6,423,305 B1 * | 7/2002 | Cauwet-Martin et al. . 424/70.19 |
| 6,468,614 B1 | 10/2002 | LeVine et al. | |
| 6,533,873 B1 | 3/2003 | Margosiak et al. | |
| 6,762,159 B2 | 7/2004 | Ishitobi | |
| 6,897,253 B2 | 5/2005 | Schmucker-Castner et al. | |
| 7,157,414 B2 | 1/2007 | Librizzi et al. | |
| 7,335,627 B1 | 2/2008 | O'Lenick et al. | |
| 7,375,064 B1 | 5/2008 | O'Lenick, Jr. | |
| 7,507,399 B1 | 3/2009 | O'Lenick, Jr. | |
| 7,547,434 B2 | 6/2009 | Tierney et al. | |
| 7,754,666 B2 | 7/2010 | Walters et al. | |
| 7,803,403 B2 | 9/2010 | Librizzi et al. | |
| 2003/0103929 A1* | 6/2003 | Maubru ..................... 424/70.16 |
| 2005/0070452 A1 | 3/2005 | Librizzi et al. | |
| 2006/0014662 A1 | 1/2006 | Kohut et al. | |
| 2006/0257348 A1 | 11/2006 | Walters et al. | |
| 2007/0111910 A1 | 5/2007 | Walters et al. | |
| 2008/0112913 A1 | 5/2008 | Librizzi et al. | |
| 2008/0113895 A1 | 5/2008 | Tamareselvy et al. | |
| 2009/0053337 A1 | 2/2009 | Hansenne et al. | |

FOREIGN PATENT DOCUMENTS

| | | |
|---|---|---|
| DE | 198 18 410 A1 | 10/1999 |
| DE | 10 2008 059445 A1 | 6/2010 |
| EP | 1 010 422 A2 | 6/2000 |
| EP | 1 559 774 A1 | 8/2005 |
| WO | WO 99/21530 A1 | 5/1999 |
| WO | WO 2008/060997 A1 | 5/2008 |
| WO | WO 2009/016375 A2 | 5/2009 |

OTHER PUBLICATIONS

Rohm and Haas Company (Dow Personal Care) "ACULYN 33 Rheology Modifier/Stablilizer", Brochure (Sep. 2002).
PCT Search Report dated Jan. 11, 2012, for PCT Application No. PCT/US20111/041611.
European Communication dated May 31, 2012 from Application No. 11194698 EP Search Report.

* cited by examiner

*Primary Examiner* — Necholus Ogden, Jr.

(57) ABSTRACT

The methods and compositions of this invention relate to compositions having low irritation characteristics in combination with one or more additional characteristics, for example, relatively high clarity, relatively high foaming, and/or combinations thereof, as well as methods of making and using such compositions. These compositions have low pH values and are useful in cleansing the skin.

11 Claims, No Drawings

US 8,343,902 B2

LOW-IRRITATING, CLEAR CLEANSING COMPOSITIONS WITH RELATIVELY LOW PH

FIELD OF THE INVENTION

The methods and compositions of this invention relate to compositions having low irritation characteristics in combination with one or more additional characteristics, for example, relatively high clarity, relatively high foaming, and/or combinations thereof, as well as methods of making and using such compositions. These compositions have low pH values and are useful in cleansing the skin.

BACKGROUND OF THE INVENTION

Synthetic surfactant detergents, such as cationic, anionic, amphoteric, and non-ionic surfactants, are used widely in a variety of detergent and cleansing compositions to impart cleansing properties thereto. In addition, in certain compositions such as personal care compositions including shampoos and washes, it may be desirable to use combinations and levels of surfactants sufficient to achieve relatively high levels of foam volume and/or foam stability.

However, as is recognized in the art, synthetic detergents tend to be irritating to the skin and eyes. As concentrations of such detergents increase in personal care compositions so as to impart increased cleansing and foaming properties to these compositions, the irritation associated with such compositions also tends to increase, making them undesirable for use on or near the skin and/or eyes.

Certain attempts to produce milder cleansing compositions have included combining relatively low amounts of anionic surfactants (which tend to be relatively high-foaming but also relatively highly irritating) with relatively lower irritating surfactants such as nonionic and/or amphoteric surfactants. See, e.g. U.S. Pat. No. 4,726,915. Another approach to producing mild cleansing compositions is to associate the anionic surfactants with amphoteric or cationic compounds in order to yield surfactant complexes. See, e.g., U.S. Pat. Nos. 4,443,362; 4,726,915; 4,186,113; and 4,110,263. Disadvantageously, mild cleansing compositions produced via both of such methods tend to suffer from relatively poor foaming and cleansing performance.

It has further been recognized that, for certain uses, consumers desire cleansing compositions to be relatively clear. In particular, clear compositions are often used advantageously to provide an aesthetic indication of purity to the consumer. However, a number of ingredients commonly used in conventional personal care compositions, including, for example, polymeric thickeners, tend to cause the compositions to become cloudy or opaque. It is not readily predictable which combinations of polymers, surfactants and other optional ingredients may be combined to create compositions that are suitable for use as cleansers and also exhibit high clarity.

Another complicating factor with respect to creating clear compositions is that certain polymeric thickeners require higher pH to maintain clarity and stability in personal care compositions.

U.S. Pat. No. 6,897,253 ('253) describes a substantially crosslinked alkali-swellable acrylate copolymer rheology modifier, water, an alkaline material, and an effective amount of surfactant so that a substantially insoluble compound is stabilized or suspended. The disclosed polymeric rheology modifiers do not start to build substantial viscosity until a pH of about 5 or 6 or higher is achieved. To formulate a composition with a lower pH is difficult but '253 discusses a "Back-Acid" thickening method to achieve clear cleansing systems with an acrylate rheology modifier and high surfactant concentrations (greater than about 9.8% actives) at low pH (about pH 4.5-5). This method involves formulating at a higher pH to obtain the appropriate viscosity and stability and then slowly lowering the pH with an organic acid.

US 2008/0113895 sets forth the use of low molecular weight acrylic polymers with the anionic surfactants sodium laureth sulfate and sodium trideceth sulfate for mild cleansing systems. Clear cleansing system are achieved, but only at pH of greater than 6.5.

US 2008/0112913 describes the use of low molecular weight acrylic polymers for irritation mitigation and points out the difficulty in creating clear cleansing systems with low molecular weight hydrophobically modified polymers. While clear systems are achieved with low molecular weight acrylic polymer combined with either sodium laureth sulfate, sodium trideceth sulfate, or cocamidopropyl betaine, the pH of the compositions must be 6.5.

It is desirable to formulate skin care compositions, including cleansing compositions, to be as mild as possible to the skin and eyes. One way in which to achieve this goal is by having a composition that has pH that is compatible with the skin and eyes. In addition, there is a need for the compositions to exhibit relatively high clarity, desirable foam properties and/or other desirable aesthetic properties. Additional aspects of skin care compositions involve safety and compatible preservative systems.

The ingredients of the skin care compositions of this invention may also require certain pH parameters. For example, certain active ingredients such salicylic acid require low pH for activity.

Some preservative systems, preservatives that function in their acidic form and not in there salt form, e.g. sodium benzoate or potassium sorbate, require a low composition pH for efficacy. The efficiency of the preservative decreases with increasing pH, dependent upon the pKa of the preservative. Therefore it is desirable to formulate at low pH to provide maximum efficiency while maintaining a pH compatible with the skin and eyes.

Additionally, it is desirable to formulate compositions to have a pH neutral to the skin, from about 5 to about 6. Cleansers having a pH below that of skin (between about 4 and about 5) may be desired in order to lower the pH of skin for enhanced enzyme function and to alter the skin microflora.

The skin care compositions of this invention have low pH yet have high clarity. The compositions have low irritation characteristics and are clear.

SUMMARY OF THE INVENTION

The skin cleansing compositions of this invention preferably comprise, consist essentially of and consist of:
 (a) a low molecular weight, non-crosslinked, linear acrylic copolymer; and
 (b) at least one non-ethoxylated anionic surfactant comprising more than about 2 weight percent of the skin care composition;
  wherein the total surfactant load of said skin cleansing composition is not greater than about 9 weight percent of the skin cleansing composition; the pH of said skin cleansing composition is about 6.2 or less; and the skin cleansing composition has a count of 70 kcts/s or less in a light scattering test.

In addition, the skin cleansing compositions of this invention preferably comprise, consist essentially of and consist of:

(a) a low molecular weight, non-crosslinked, linear acrylic copolymer; and
(b) at least one non-ethoxylated anionic surfactant comprising more than about 2 weight percent of the skin cleansing composition;
(c) wherein the total surfactant load of said skin cleansing composition is not greater than about 9 weight percent of the skin cleansing composition; the pH of said skin cleansing composition is about 6.2 or less; and the transmittance of said skin cleansing composition is greater than about 90%.

The methods of this invention also relate to imparting clarity to skin cleansing compositions containing non-ethoxylated anionic surfactants by utilizing skin cleansing compositions containing low molecular weight, non-crosslinked, linear acrylic copolymers wherein the total surfactant load of said skin cleansing composition is not greater than about 9 weight percent of the skin cleansing composition; the pH of said skin care composition is about 6.2 or less. This invention further relates to a method of using such methods and compositions on the skin.

DETAILED DESCRIPTION OF THE INVENTION

Applicants have herein discovered that the compositions of the present invention exhibit a unique and unexpected combination of properties including relatively low irritation and relatively high clarity at a lower than expected pH, a pH that is compatible with skin. This makes the present invention ideal for skin care, including baby and infant skin, cosmetic or cleansing compositions. The compositions include a low molecular weight, non-crosslinked, linear acrylic copolymer and at least one anionic surfactant. Surprisingly, using a select group of surfactants to bind with the low molecular weight, non-crosslinked, linear acrylic copolymer, results in a composition that is clear at a pH lower than previously thought would be possible.

As used herein, the term "low pH" shall include pH measurements of less than about 6 as determined by ASTM method E70-07 Standard Test Method for pH of Aqueous Solutions With the Glass Electrode. In a preferred embodiment, the pH range is between about 3.5 and about 6.2. In a more preferred embodiment, the pH range is between about 4 and about 6. In a most preferred embodiment, the pH range is between about 4.5 and about 5. It was previously known that pH also affects certain preservative and surfactant systems. For example, a high pH reduces the efficacy of preservative system. For example, as detailed in below, an organic acid preservative system may become ineffective if the appropriate pH is not maintained.

As used herein, the term "clear composition" shall mean that the composition shall have a light transmittance of greater than about 90%, more preferably greater than about 90.5%, and most preferably greater than about 95% as determined by the Clarity Test as defined in the methods section. As used herein, the term "clear composition" shall mean that the composition shall have a count rate of less than about 70 kcts/s, more preferably less than about 50 kcts/s kcts/s, and most preferably less than about 40 kcts/s, as determined by the Light Scattering Test as defined in the methods section.

Polymeric Material

As used herein the term "low molecular weight" polymer refers to a polymer having a number average molecular weight ($M_n$) as measured by gel permeation chromatography (GPC) calibrated with a poly(methyl methacrylate) (PMMA) standard of about 100,000 or less. In certain preferred embodiments, low-molecular weight polymers are those having molecular weight ranges of from about 5,000 to about 80,000 $M_n$, more preferably from about 10,000 to about 50,000 $M_n$, and more preferably between about 15,000 and 40,000 $M_n$.

The polymeric material useful in the methods of this invention is preferably a composition suitable for associating anionic and/or amphoteric surfactant thereto and is a non-crosslinked, linear acrylic copolymer that mitigates the impaired dermal barrier damage typically associated with surfactant systems without substantially increasing viscosity build. The non-crosslinked, linear polymers are preferably of low molecular weight having a number average molecular weight of 100,000 or less as measured by gel permeation chromatography (GPC) calibrated with a poly(methyl methacrylate) (PMMA) standard (as used herein, unless otherwise specified, all number average molecular weights ($M_n$) refer to molecular weight measured in such manner). The copolymeric mitigant is polymerized from at least two monomeric components. The first monomeric component is selected from one or more α,β-ethylenically unsaturated monomers containing at least one carboxylic acid group. This acid group can be derived from monoacids or diacids, anhydrides of dicarboxylic acids, monoesters of diacids, and salts thereof. The second monomeric component is hydrophobically modified (relative to the first monomeric component) and is selected from one or more α,β-ethylenically unsaturated non-acid monomers containing a $C_1$ to $C_9$ alkyl group, including linear and branched $C_1$ to $C_9$ alkyl esters of (meth)acrylic acid, vinyl esters of linear and branched $C_1$ to $C_{10}$ carboxylic acids, and mixtures thereof. In one aspect of the invention the second monomeric component is represented by the formula:

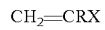

wherein R is hydrogen or methyl; X is —C(O)OR$^1$ or —OC(O)R$^2$; R$^1$ is linear or branched $C_1$ to $C_9$ alkyl; and R$^2$ is hydrogen or linear or branched $C_1$ to $C_9$ alkyl. In another aspect of the invention R$^1$ and R$^2$ is linear or branched $C_1$ to $C_8$ alkyl and in a further aspect R$^1$ and R$^2$ are linear or branched $C_2$ to $C_5$ alkyl.

Exemplary first monomeric components include (meth)acrylic acid, itaconic acid, citraconic acid, maleic acid, fumaric acid, crotonic acid, aconitic acid, and mixtures thereof. Exemplary second monomeric components include ethyl (meth)acrylate, butyl (meth)acrylate, 2-ethylhexyl (meth)acrylate, vinyl formate, vinyl acetate, 1-methylvinyl acetate, vinyl propionate, vinyl butyrate, vinyl 2-ethylhexanoate, vinyl pivalate, vinyl neodecanoate, and mixtures thereof. As used herein, the term "(meth)acrylic" acid and "(meth)acrylate" are meant to include the corresponding methyl derivatives of acrylic acid and the corresponding alkyl acrylate For example, "(meth)acrylic" acid refers to acrylic acid and/or methacrylic acid and "(meth)acrylate" refers to alkyl acrylate and/or alkyl methacrylate.

More preferably, said first monomeric component is selected from the group consisting of (meth)acrylic acid and said second monomeric component is selected from the group consisting of at least one C1 to C9 alkyl (meth)acrylate.

The non-crosslinked, linear acrylic copolymer mitigants of the invention can be synthesized via free radical polymerization techniques known in the art. In one aspect of the invention, the amount of the first monomeric component to the second monomeric component utilized ranges from about 20:80 wt. % to about 50:50 wt. %, based on the total weight of all of the monomers in the polymerization medium. In another aspect the weight ratio of the first monomeric component to the second monomeric component is about 35:65 wt. %, and in a further aspect the weight ratio of first monomeric component to second monomeric component is about 25:75 wt. %, all based on the total weight of all monomers in the polymerization medium.

In another aspect emulsion polymerization techniques can be used to synthesize the non-crosslinked, linear acrylic copolymer mitigants of the invention. In a typical emulsion polymerization, a mixture of the disclosed monomers is added with mixing agitation to a solution of emulsifying surfactant, such as, for example, an anionic surfactant (e.g., fatty alcohol sulfates or alkyl sulfonates), in a suitable amount of water, in a suitable reactor, to prepare a monomer emulsion. The emulsion is deoxygenated by any convenient method, such as by sparging with nitrogen, and then a polymerization reaction is initiated by adding a polymerization catalyst (initiator) such as sodium persulfate, or any other suitable addition polymerization catalyst, as is well known in the emulsion polymerization art. The polymerization medium is agitated until the polymerization is complete, typically for a time in the range of about 4 to about 16 hours. The monomer emulsion can be heated to a temperature in the range of about 70 to about 95° C. prior to addition of the initiator, if desired. Unreacted monomer can be eliminated by addition of more catalyst, as is well known in the emulsion polymerization art. The resulting polymer emulsion product can then be discharged from the reactor and packaged for storage or use. Optionally, the pH or other physical and chemical characteristics of the emulsion can be adjusted prior to discharge from the reactor. Typically, the product emulsion has a total solids content in the range of about 10 to about 50 wt. %. Typically, the total polymer content (polymer solids) of the product emulsion is in the range of about 15 to about 45 wt. %, generally not more than about 35 wt. %.

In one aspect, the number average molecular weight ($M_n$) of the linear copolymeric mitigants of the present invention as measured by gel permeation chromatography (GPC) calibrated with a poly(methyl methacrylate) (PMMA) standard is 100,000 or less. In another aspect of the invention, the molecular weight ranges between about 5,000 and about 80,000 $M_n$, in a further aspect between about 10,000 and 50,000 $M_n$, and in a still further aspect between about 15,000 and 40,000 $M_n$.

In one aspect of the invention, the linear copolymeric mitigants have a viscosity of 500 mPa·s or less (Brookfield RVT, 20 rpm, spindle no. 1) at a 5 wt. % polymer solids concentration in deionized water and neutralized to pH 7 with an 18 wt. % NaOH solution. The viscosity can range from about 1 to about 500 mPa·s in another aspect, from about 10 to about 250 mPa·s in a further aspect, and from about 15 to about 150 mPa·s in a still further aspect.

Preferably, the low molecular weight, non-crosslinked linear acrylic copolymer is potassium acrylates copolymer.

Any of a variety of non-ethoxylated anionic surfactants may be combined with a polymeric material of the present invention to form a cleansing composition according to preferred embodiments of the present methods. Non-ethoxylated anionic surfactants are surfactants that have a negative charge and do not contain any ethoxylated segments, that is to say there are no —(C—C—O)$_v$— segments on the surfactants. According to certain embodiments, suitable non-ethoxylated anionic surfactants include those selected from the following classes of surfactants: alkyl sulfates, alkyl sulfonates, alkyl monoglyceride sulfonates, alkylaryl sulfonates, alkyl sulfosuccinates, alkyl sulfosuccinamates, alkyl carboxylates, fatty alkyl sulfoacetates, alkyl phosphates, acylglutamates, sarcosinates, taurates, and mixtures of two or more thereof Examples of certain preferred anionic surfactants include:

alkyl sulfates of the formula

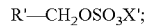

alkyl monoglyceride sulfates of the formula

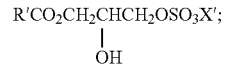

alkyl monoglyceride sulfonates of the formula

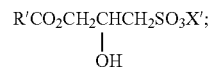

alkyl sulfonates of the formula

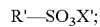

alkylaryl sulfonates of the formula

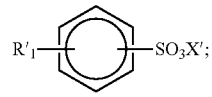

alkyl sulfosuccinates of the formula:

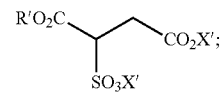

alkyl phosphates
wherein
R' is an alkyl group having from about 7 to about 22, and preferably from about 7 to about 16 carbon atoms,
R'$_1$ is an alkyl group having from about 1 to about 18, and preferably from about 8 to about 14 carbon atoms,
R'$_2$ is a substituent of a natural or synthetic I-amino acid,
X' is selected from the group consisting of alkali metal ions, alkaline earth metal ions, ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and
w is an integer from 0 to 20; and mixtures thereof.

According to certain embodiments, the anionic surfactant of the present invention is preferably a non-ethoxylated SO$_x$ anionic surfactant conforming to the structure below

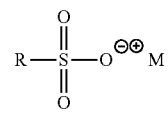

Where SO$_3^-$ is the anionic hydrophilic group, M$^+$ is a monovalent cation (such as NH$_4^+$, Na$^+$, K$^+$, (HOCH$_2$CH$_2$)$_3$ $N^+$, etc.), and R comprises any of a broad range of hydrophobic groups and optionally, a) functional groups to link the hydrophilic and hydrophobic moieties and/or b) additional hydrophilic groups. Examples include:

Alkyl sulfonates, where R equals $C_6$-$C_{20}$ alkyl, (linear or branched, saturated or unsaturated), preferably $C_{10}$-$C_{18}$, and most preferably $C_{12}$-$C_{17}$. Specific examples include Sodium C13-C17 Alkane Sulfonate (R=$C_{13}$-$C_{17}$ alkyl, $M^+$=$^{Na+}$) and Sodium C14-C17 Alkyl Sec Sulfonate (R=s-$C_{13}$-$C_{17}$ alkyl, $M^+$=$Na^+$)

Alpha olefin sulfonates, where R equals a mixture of

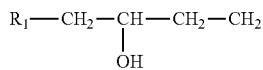

and

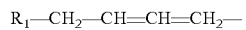

where $R_1$=$C_4$-$C_{16}$ alkyl or mixtures thereof, preferably C6-C12, more preferably C8-C12, and most preferably C10-C12. Specific examples include Sodium C12-14 Olefin Sulfonate ($R_1$=$C_8$-$C_{10}$ alkyl, $M^+$=$Na^+$) and Sodium C14-16 Olefin Sulfonate ($R_1$=$C_{10}$-$C_{12}$ alkyl, $M^+$=$Na^+$).

Alkyl sulfate esters, where $R_1$=$C_6$-$C_{20}$,

(linear or branched, saturated or unsaturated), preferably C12-C18, more preferably C12-C16, and most preferably C12-C14. Specific examples include Ammonium Lauryl Sulfate ($R_1$=lauryl, $C_{12}H_{25}$, $M^+$=$NH_4^+$), Sodium Lauryl Sulfate ($R_1$=lauryl, $C_{12}H_{25}$, $M^+$=$Na^+$), and Sodium Cocosulfate ($R_1$=coco alkyl, $M^+$=$Na^+$).

Any suitable amounts of polymeric material and surfactants may be used in accord with the compositions and methods of this invention. In certain preferred embodiments, the compositions of this invention comprise, consist essentially of and consist of from greater than zero to about 6 weight percent of polymeric material (based on active amount of polymeric material in the total weight of composition). In certain more preferred embodiments, the compositions comprise from about 0.1 to about 4.5 weight percent of polymeric material, more preferably from about 0.1 to about 3.5 weight percent of polymeric material, and even more preferably from about 0.2 to about 2.5 weight percent of polymeric material.

In certain preferred embodiments, the compositions of this invention comprise, consist essentially of and consist of from greater than about 2 to less than about 9 weight percent of anionic surfactants based on total active amount of surfactant(s) in the total weight of composition. In certain more preferred embodiments, the compositions comprise from about 2 to about 7 weight percent of surfactants. Preferred embodiment formulas have from about 2 to about 5 weight percent total surfactant.

The non-crosslinked, linear acrylic copolymers useful in the compositions of this invention can be synthesized via free radical polymerization techniques known in the art. In one aspect of the invention, the amount of the first monomeric component to the second monomeric component utilized ranges from about 20:80 wt. % to about 50:50 wt. %, based on the total weight of all of the monomers in the polymerization medium. In another aspect the weight ratio of the first monomeric component to the second monomeric component is about 35:65 wt. %, and in a further aspect the weight ratio of first monomeric component to second monomeric component is about 25:75 wt. %, all based on the total weight of all monomers in the polymerization medium.

The cleansing compositions produced, as well as any of the compositions containing polymeric material and at least one anionic that are combined in the combining step according to the present methods may further comprise any of a variety of other components nonexclusively including additives which enhance the appearance, feel and fragrance of the compositions, such as colorants, fragrances, preservatives, pH adjusting agents and the like.

Any of a variety of commercially available secondary conditioners, such as volatile silicones, which impart additional attributes, such as gloss to the hair are suitable for use in this invention. In one embodiment, the volatile silicone conditioning agent has an atmospheric pressure boiling point less than about 220° C. The volatile silicone conditioner may be present in an amount of from about 0 percent to about 3 percent, e.g. from about 0.25 percent to about 2.5 percent or from about 0.5 percent to about 1.0 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids.

Any of a variety of commercially available humectants, which are capable of providing moisturization and conditioning properties to the personal cleansing composition, are suitable for use in the present invention. The humectant may be present in an amount of from about 0 percent to about 10 percent, e.g. from about 0.5 percent to about 5 percent or from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, and mixtures thereof; 2) polyalkylene glycol of the formula: HO—(R"O)$_b$—H, wherein R" is an alkylene group having from about 2 to about 3 carbon atoms and b is an integer of from about 2 to about 10; 3) polyethylene glycol ether of methyl glucose of formula $CH_3$—$C_6H_{10}O_5$—$(OCH_2CH_2)_c$—OH, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL" and is present in an amount, based upon the total weight of the composition, from about 0 to about 0.5 percent or from about 0.05 percent to about 0.25 percent.

Suitable preservatives include organic acid preservatives may include benzoic acid and alkali metal and ammonium salts thereof (e.g. sodium benzoate), sorbic acid and alkali metal and ammonium salts thereof (e.g. potassium sorbate), p-Anisic acid and alkali metal and ammonium salts thereof, and salicylic acid and alkali metal and ammonium salts thereof. The pH of the composition may be adjusted to the appropriate acidic value using any cosmetically acceptable organic or inorganic acid, such as citric acid, acetic acid, glycolic acid, lactic acid, malic acid, tartaric acid, or hydrochloric acid.

In one embodiment of the composition, sodium benzoate is present in the composition in an amount, based upon the total weight of the composition, from about 0 to about 0.5 percent.

In another embodiment, potassium sorbate is present in the composition in an amount, based upon the total weight of the composition, from about 0 to about 0.6 percent, more preferably from about 0.3 to about 0.5 percent.

The methods of this invention may further comprise any of a variety of steps for mixing or introducing one or more of the optional components described hereinabove with or into a composition comprising a polymeric material before, after, or simultaneously with the combining step described above. While in certain embodiments, the order of mixing is not critical, it is preferable, in other embodiments, to pre-blend certain components, such as the fragrance and the nonionic surfactant before adding such components into a composition comprising a polymeric material and/or an anionic surfactant.

The cleansing methods of the present invention may further comprise any of a variety of additional, optional steps associated conventionally with cleansing hair and skin including, for example, lathering, rinsing steps, and the like.

Although applicants do not wish to be bound by or to any particular theory of operation, it is believed that surfactant associated with the low molecular weight hydrophobically-modified polymer (hm-polymer) is more stable than surfactants that exist as a micelle. Thus, surfactant contained in a micelle structure more readily disperses out of the micelle than it does when associated with low molecular weight hydrophobically-modified polymer.

The foregoing information regarding low molecular weight hydrophobically-polymers as well as compositions that may be useful in the methods of this invention are set forth in US2008/0112913, US2006/0257348, and US20070111910, all of which are hereby incorporated herein by reference.

The methods and compositions of this invention illustratively disclosed herein suitably may be practiced in the absence of any component, ingredient, or step which is not specifically disclosed herein.

Several examples are set forth below to further illustrate the nature of the invention and the manner of carrying it out. However, the invention should not be considered as being limited to the details thereof.

Methods

Clarity Test:

The clarity of each sample was measured via the Clarity Test, the procedure for which comprises preparing a 1 cm cell sample of the composition to be measured and measuring the % light transmittance associated with such sample using an Agilent 8453 UV-Visible Spectrophotometer with a 1 cm cell at a wavelength of 800 nm. The clarity was determined for each cleansing composition without dilution. The results are reported as % T, the % transmittance through cleansing composition in the 1 cm cell.

Light Scattering Test:

The clarity of a cleanser is determined by colloidal assembles that scatter light. A cleanser that is clearer typically will have only small colloidal assemblies. Larger colloidal assemblies, on the order of ⅓ the wavelength of light, will scatter light and produce a hazy or turbid solution.

The cleanser samples were analyzed using a Zetasizer Nano ZS DLS instrument (Malvern Instruments, Inc., Southborough, Mass.) operating at 25.0° C. The instrument was integrated with the Malvern Dispersion Technology Software. The unfiltered sample solutions was diluted to 3% and dispensed into cuvettes (12 mm Square Polystyrene Cuvettes, DTS0012) to the 10 mm mark, and covered. The measurements were done at attenuation 7, with a 4 mW He—Ne, 633 nm laser at position 4.65 mm. The temperature was kept constant at 25 degrees Celsius. Measurements were done in 3 repetitions and 11 runs each.

The laser (at 633 nm) is incident on the cleansing composition and scatters from colloidal assemblies back to the detector. A hazy cleansing solution will have more and larger colloidal particles therefore producing more scattering to the detector and a higher count rate.

Example 1

Comparatives C1-C4

Preparation of Cleansing Compositions

The cleansing compositions of C1-C4 were prepared according to the materials and amounts listed in Table 1.

TABLE 1

| Trade Name | INCI name | C1 w/w % | C2 w/w % | C3 w/w % | C4 w/w % |
|---|---|---|---|---|---|
| Cedepal TD-403 (30%) | Sodium Trideceth Sulfate | 2.70 | 2.70 | 2.70 | 2.70 |
| Tegobetaine L-7V (30%) | Cocamidopropyl Betaine | 2.70 | 2.70 | 2.70 | 2.70 |
| Merquat S | Polyquaternium-7 | 0.01 | 0.01 | 0.01 | 0.01 |
| Versene 100 XL | Tetrasodium EDTA | 0.10 | 0.10 | 0.10 | 0.10 |
| Aqua SF-1 (30%) | Acrylates Copolymer | — | 1.80 | — | — |
| Ex-968 (30%) | Potassium Acrylates Copolymer | — | — | 1.80 | — |
| Inutec SP-1 | Inulin Lauryl Carbamate | — | — | — | 1.80 |
| 20% NaOH | Sodium Hydroxide | qs | qs | qs | qs |
| Deionized water | Water | qs | qs | qs | qs |

*expressed in % w/w actives

Each of the compositions of Table 1 was independently prepared as follows: Water (50.0 parts) was added to a beaker. The following ingredients were then added thereto independently with mixing until each respective resulting mixture was homogenous: the hm-polymer (Ex. 968, Aqua SF-1, Inutec SP-1, etc. depending on the example), Cedepal TD403MF-D, Tegobetaine L7-V, Merquat S, Versene 100XL, and Nipasept. The pH of the resulting solution was then adjusted with a 20% solution of Citric Acid or Sodium hydroxide solution until the final desired pH was obtained. The remainder of the water was then added thereto. Formulas with the same components, but different pH's were all made independently.

Example 2

Clarity Results for Samples C1-C4 at Different pH's

The clarity of compositions of C1-C4 determined according to the Clarity test.

TABLE 2

| Ex | hm-Polymer added | pH | Clarity (% T) |
|---|---|---|---|
| C1 | No polymer | 6.3 - 6.6 | 99.1 |
| C2 | Acrylates copolymer | 6.3 - 6.6 | 88.3 |

TABLE 2-continued

| Ex | hm-Polymer added | pH | Clarity (% T) |
|---|---|---|---|
| C3 | Potassium Acrylates Copolymer | 6.3 - 6.6 | 98.8 |
| C4 | Inulin Lauryl Carbamate | 6.3 - 6.6 | 37.1 |
| C2 | Acrylates copolymer | 4.0 | 18.0 |
| C3 | Potassium Acrylates Copolymer | 4.0 | 24.1 |
| C4 | Inulin Lauryl Carbamate | 4.0 | 36.4 |

Table 2 shows the results of the clarity test of a series of cleansing compositions containing a series of low molecular weight hm-polymers and the surfactants Sodium Trideceth Sulfate and Cocamidopropyl Betaine as described in Table 1. While the clarity of the cleansing compositions are clear (i.e. have a % Transmittance as measured by the Clarity test greater than about 90%) at high pH, around about 6.3, the clarity is much lower at lower pH. In US 2008/0112913, the cleansing systems contained sodium trideceth sulfate or sodium laureth sulfate. While US 2008/0112913 shows clear cleansing systems with a low molecular weight linear acrylic polymer and these surfactants, when these same systems are prepared at lower pH (below about a pH of 6.2) the cleansing systems lose clarity and become hazy and translucent.

Example 3

Comparatives C5-C7

Preparation of Cleansing Compositions

The cleansing compositions of C5-C7 were prepared according to the materials and amounts listed in Table 3

TABLE 3

| INCI name | C5 w/w % | C6 w/w % | C7 w/w % |
|---|---|---|---|
| Sodium Benzoate | 0.50 | 0.50 | 0.50 |
| Potassium Acrylates Copolymer | 1.80 | 1.80 | 1.80 |
| Cocamidopropyl hydroxysultaine | — | 3.40 | — |
| Decyl Glucoside | — | — | 3.70 |
| Sodium hydroxide | q.s. | q.s. | q.s. |
| Water | q.s. | q.s. | q.s. |

*expressed in w/w% actives

Each of the compositions of Table 3 was independently prepared as follows: Water (50.0 parts) was added to a beaker. The following ingredients were then added thereto independently with mixing until each respective resulting mixture was homogenous: the hm-polymer Potassium Acrylates Copolymer (Ex. 968, Lubrizol, Brecksville, Ohio), then the surfactant Cocamidopropyl hydroxysultaine or Decyl Glucoside as called for. The pH of the resulting solution was then adjusted with a 20% solution of Sodium hydroxide or citric acid until the final desired pH was obtained. The remainder of the water was then added thereto. Formulas with the same components, but different pH's were all made independently.

Example 4

Clarity Results for Samples C5-C7 at Different pH's

The clarity of compositions of C5-C7 determined according to the Clarity test.

TABLE 4

| Ex | Surfactant Type | Surfactant | Surfactant (w/w %) | pH | Clarity (% T) |
|---|---|---|---|---|---|
| C5 | — | No surfactant: hm-polymer at 1.8% | 0 | 4.0 | 3.8 |
| C6 | Amphoteric | Cocamidopropyl hydroxysultaine | 3.4 | 5.0 | 86.9 |
| C6 | Amphoteric | Cocamidopropyl hydroxysultaine | 3.4 | 6.0 | 84.2 |
| C7 | Non-ionic | Decyl Glucoside | 3.7 | 5.0 | 86.7 |
| C7 | Non-ionic | Decyl Glucoside | 3.7 | 6.0 | 83.4 |

As shown in Table 4, the low Mw hm-polymer without surfactant, C5, at a low pH of 4.0 has a low clarity. As shown in Table 2, clear cleansing compositions are readily made at moderate pH's (pH between about 6.3-6.6) with the low molecular weight linear acrylic polymer, Potassium Acrylates Copolymer, and a number of different types of surfactant systems. Table 4 shows cleansing compositions that are not clear (% T less than about 90%) at low or high pH the low molecular weight linear acrylic polymer, Potassium Acrylates Copolymer, and the amphoteric and non-ionic surfactants, Cocamidopropyl hydroxysultaine and Decyl Glucoside respectively.

Example 5

Comparatives C8-C12 and Inventive Examples E13-E14

Preparation of Cleansing Compositions

The cleansing compositions of C8-C12 and E13-E14 were prepared according to the materials and amounts listed in Table 5.

TABLE 5

| INCI name | C8 w/w % | C9 w/w % | C10 w/w % | C11 w/w % | E13 w/w % | C12 w/w % | E14 w/w % |
|---|---|---|---|---|---|---|---|
| Sodium Benzoate | 0.50 | 0.50 | 0.50 | 0.5 | 0.5 | 0.50 | 0.50 |
| Potassium Acrylates Copolymer | 1.80 | 1.80 | 1.80 | 1.8 | 1.80 | 1.80 | 1.80 |
| Sodium Trideceth Sulfate | 2.70 | — | — | — | — | — | — |
| Sodium Laureth Sulfate | — | 0.80 | 4.60 | — | — | — | — |
| Sodium Alpha Olefin Sulfonate | — | — | — | 2.00 | 3.90 | — | — |
| Sodium Coco Sulfate | — | — | — | — | — | 1.80 | 3.70 |
| Sodium hydroxide | q.s. | q.s. | q.s. | q.s. | q.s. | q.s. | q.s. |
| Water | q.s. | q.s. | q.s. | q.s. | q.s. | q.s. | q.s. |

*expressed in w/w % actives

Each of the compositions of Table 5 was independently prepared as follows: Water (50.0 parts) was added to a beaker. The following ingredients were then added thereto independently with mixing until each respective resulting mixture was homogenous: the hm-polymer, Potassium Acrylates Copolymer (Ex. 968, Lubrizol, Brecksville, Ohio), then the surfactant Sodium Trideceth Sulfate, Sodium Laureth Sulfate, Sodium Alpha Olefin Sulfonate, or Sodium Coco Sulfate as called for. The pH of the resulting solution was then adjusted with a 20% solution Sodium hydroxide or Citric acid until the final desired pH was obtained. The remainder of the water was then added thereto. Formulas with the same components, but different pH's were all made independently.

Example 6

Clarity Results for Samples C8-C12, E13-E14 at Different pH's

The clarity of compositions of C8-C12, E13-E14 was determined according to the Clarity test.

TABLE 6

| Ex | Surfactant Type | Surfactant | Surfactant (w/w %) | pH | Clarity (% T) |
|---|---|---|---|---|---|
| C8 | Ethoxylated | Sodium Trideceth Sulfate | 2.7 | 4.0 | 81.9 |
| C9 | Ethoxylated | Sodium Laureth Sulfate | 0.8 | 4.0 | 78.8 |
| C10 | Ethoxylated | Sodium Laureth Sulfate | 4.6 | 4.0 | 88.7 |
| C11 | Anionic non-EO | Sodium Alpha Olefin Sulfonate | 2.0 | 4.0 | 86.1 |
| E13 | Anionic non-EO | Sodium Alpha Olefin Sulfonate | 3.9 | 4.0 | 95.7 |
| C12 | Anionic non-EO | Sodium Coco Sulfate | 1.8 | 4.0 | 83.7 |
| E14 | Anionic non-EO | Sodium Coco Sulfate | 3.7 | 4.0 | 99.6 |

As shown in Table 2, clear cleansing compositions are readily made at moderate pH's (pH between about 6.3 and about 6.6) with the low molecular weight linear acrylic polymer, Potassium Acrylates Copolymer, and a number of different types of surfactant systems.

However in Table 2, when these cleansing compositions are taken to low pH (below a pH of about 6.2), they lose clarity. Furthermore, the lower pH cleansing compositions C8-C10 contain a range of ethoxylated anionic surfactants over a range of levels, none of which achieve clear systems at low pH.

Cleansing compositions with the low molecular weight linear acrylic polymer, Potassium Acrylates Copolymer, and a low amount of non-ethoxylated anionic surfactant, Sodium Alpha Olefin Sulfonate and Sodium Coco Sulfate, C11 and C12, respectively, also have low clarity. However, cleansing systems with the low molecular weight linear acrylic polymer, Potassium Acrylates Copolymer, and non-ethoxylated anionic surfactant can achieve high clarity, E13 and E14. A sufficient amount of anionic surfactant, more than about 2.0% actives, is requirement to achieve a sufficiently clear formula.

Example 7

Inventive Examples E15-E21

Preparation of Cleansing Compositions

The cleansing compositions of E15-E21 were prepared according to the materials and amounts listed in Table 7.

TABLE 7

| INCI name | E15 w/w % | E16 w/w % | E17 w/w % | E18 w/w % | E19 w/w % | E20 w/w % | E21 w/w % |
|---|---|---|---|---|---|---|---|
| Sodium Benzoate | 0.5 | 0.5 | 0.5 | 0.50 | 0.50 | 0.50 | 0.5 |
| Potassium Acrylates Copolymer | 1.80 | 1.80 | 1.80 | 1.80 | 1.80 | 1.80 | 1.80 |
| Ammonium Lauryl Sulfate | 3.4 | — | — | — | — | — | — |
| Sodium Dodecyl Benzene Sulfonate | — | 8.40 | 16.8 | — | — | — | — |
| Sodium Lauryl Sulfate | — | — | — | 12.0 | — | — | — |
| Sodium Tridecyl Sulfate 303 | — | — | — | — | 3.4 | — | — |
| Sodium Tridecyl Sulfate 203 | — | — | — | — | — | 3.4 | — |
| Sodium Tridecyl Sulfate Agt | — | — | — | — | — | — | 3.4 |
| Sodium Hydroxide | q.s. | q.s. | q.s. | q.s. | q.s. | q.s. | q.s. |
| Water | q.s. | q.s. | q.s. | q.s. | q.s. | q.s. | q.s. |

*expressed in % w/w actives

Each of the compositions of Table 7 was independently prepared as follows: Water (50.0 parts) was added to a beaker. The following ingredients were then added thereto independently with mixing until each respective resulting mixture was homogenous: the hm-polymer, Potassium Acrylates Copolymer (Ex. 968, Lubrizol, Brecksville, Ohio), then the surfactant Ammonium Lauryl Sulfate, Sodium Dodecyl Benzene Sulfonate, Sodium Lauryl Sulfate, or Sodium Tridecyl Sulfate as called for. The pH of the resulting solution was then adjusted with a 20% solution Sodium hydroxide or Citric acid until the final desired pH was obtained. The remainder of the water was then added thereto. Formulas with the same components, but different pH's were all made independently.

Example 8

Clarity Results for Inventive Examples E13-E21 at Different pH's

The clarity of compositions of E13-E21 determined according to the Clarity test.

TABLE 8

| Ex | Surfactant Type | Surfactant | Surfactant (w/w %) | pH | Clarity (% T) |
|---|---|---|---|---|---|
| E13 | Anionic non-EO | Sodium Alpha Olefin Sulfonate | 3.9 | 4.0 | 95.7 |

TABLE 8-continued

| Ex | Surfactant Type | Surfactant | Surfactant (w/w %) | pH | Clarity (% T) |
|---|---|---|---|---|---|
| E13 | Anionic non-EO | Sodium Alpha Olefin Sulfonate | 3.9 | 5.0 | 99.4 |
| E13 | Anionic non-EO | Sodium Alpha Olefin Sulfonate | 3.9 | 6.5 | 99.4 |
| E14 | Anionic non-EO | Sodium Coco Sulfate | 3.7 | 4.0 | 99.6 |
| E14 | Anionic non-EO | Sodium Coco Sulfate | 3.7 | 5.0 | 99.9 |
| E14 | Anionic non-EO | Sodium Coco Sulfate | 3.7 | 6.5 | 99.6 |
| E15 | Anionic non-EO | Ammonium Lauryl Sulfate | 3.4 | 4.0 | 100.0 |
| E15 | Anionic non-EO | Ammonium Lauryl Sulfate | 3.4 | 5.0 | 100.0 |
| E15 | Anionic non-EO | Ammonium Lauryl Sulfate | 3.4 | 6.5 | 100.0 |
| E16 | Anionic non-E0 | Sodium dodecyl benzene sulfonate | 8.4 | 4.0 | 90.6 |
| E17 | Anionic non-E0 | Sodium dodecyl benzene sulfonate | 16.8 | 4.0 | 98.2 |
| E17 | Anionic non-E0 | Sodium dodecyl benzene sulfonate | 16.8 | 5.0 | 99.7 |
| E18 | Anionic non-E0 | Sodium Lauryl Sulfate | 12.0 | 5.0 | 99.8 |
| E18 | Anionic non-E0 | Sodium Lauryl Sulfate | 12.0 | 6.5 | 97.9 |
| E19 | Anionic non-E0 | Sodium Tridecyl Sulfate 303 | 3.4 | 4.5 | 98.9 |
| E19 | Anionic non-E0 | Sodium Tridecyl Sulfate 303 | 3.4 | 6.5 | 100 |
| E20 | Anionic non-E0 | Sodium Tridecyl Sulfate 203 | 3.4 | 4.5 | 99.4 |
| E20 | Anionic non-E0 | Sodium Tride0cyl Sulfate 203 | 3.4 | 6.5 | 99.9 |
| E21 | Anionic non-E0 | Sodium Tridecyl Sulfate Agt | 3.4 | 4.5 | 97.4 |
| E21 | Anionic non-E0 | Sodium Tridecyl Sulfate Agt | 3.4 | 6.5 | 98.3 |

The previous cleansing compositions, C1-C4 and C6-C10, shown have contained amphoteric, non-ionic and/or ethoxylated anionic surfactants, and all of these cleansing compositions at lower pH, below about 6.2, have had low clarity. All of the cleansing compositions in Table 8, E13-E21, contain the low Mw hm-polymer, Potassium Acrylates copolymer, and a range of non-ethoxylated anionic surfactants at levels above 2.0% actives, and all of these cleansing compositions have high clarity. Surprisingly we find that in cleansing compositions with low MW hm-polymer and non-ethoxylated surfactants, at levels between about 9.0 wt % actives and about 2.0 wt % actives, the clarity of the compositions to be high even at low pH.

Example 9

Light Scattering Results for Selected Samples: E15, E17, E18 and C8, C10, C11

The count rate was determined at attenuations of 7:

TABLE 9

| Ex | Surfactant | pH | Count rate (@ 7) kcts/s |
|---|---|---|---|
| E15 | Ammonium Lauryl Sulfate | 4.0 | 36.7 +/− 0.4 |
| E17 | Sodium dodecyl benzene sulfonate | 4.0 | 18.8 +/− 0.2 |
| E18 | Sodium Lauryl Sulfate | 5.0 | 10.1 +/− 0.2 |
| C8 | Sodium Trideceth Sulfate | 4.0 | 197 +/− 3.6 |
| C10 | Sodium Laureth Sulfate | 4.0 | 85.8 +/− 0.2 |
| C11 | Sodium alpha Olefin Sulfonate | 4.0 | 80.2 +/− 1.6 |

Table 9 shows the results of the Light Scattering test. A higher count rate indicates the cleanser has more or larger assemblies that scatter more light. The three examples, E15, E17, and E18 were shown in the Light Scattering test to have a low count rate. In contrast, the comparatives, C8, C10, and C11, have in the Light Scattering test a high count rate (greater than about 70 kcts/s).

What is claimed is:

1. A skin cleansing composition comprising:
   (a) a low molecular weight, non-crosslinked, linear acrylic copolymer derived from at least one first monomeric component selected from the group consisting of (meth)acrylic acid and at least one second monomeric component selected from the group consisting of one or more $C_1$ to $C_9$ alkyl (meth)acrylates, wherein the low molecular weight copolymer has a number average molecular weight of about 100,000 or less; and
   (b) at least one non-ethoxylated anionic surfactant comprising more than about 2 weight percent of the skin cleansing composition;
   wherein the total surfactant load of said skin cleansing composition is not greater than about 9 weight percent of the skin cleansing composition; the pH of said skin cleansing composition is about 6.2 or less; and the skin cleansing composition has a count of 70 kcts/s or less in a light scattering test.

2. A skin cleansing composition according to claim 1 wherein said total surfactant load of said skin cleansing composition is not greater than about 7 weight percent of the skin cleansing composition.

3. A skin cleansing composition according to claim 1 wherein the transmittance of said skin cleansing composition is greater than about 90%.

4. A skin cleansing composition according to claim 1 wherein the pH of said skin cleansing composition is between about 4 and about 6.2.

5. A skin cleansing composition according to claim 1 wherein said skin cleansing composition contains no more than about 5 weight percent of ethoxylated surfactant.

6. A skin cleansing composition according to claim 1 wherein said composition has a count of 50 kcts/s or less.

7. A skin cleansing composition according to claim 6 wherein said composition has a count of 40 kcts/s or less.

8. A skin cleansing composition according to claim 5 wherein said composition contains no more than about 1 weight percent of ethoxylated surfactant.

9. A skin cleansing composition according to claim 1 wherein said low molecular weight, non-cross-linked, linear acrylic copolymer comprises a copolymer containing a first monomeric component selected from the group consisting of one or more α,β-ethylenically unsaturated monomers containing at least one carboxylic acid group; and a second, hydrophobically modified monomeric component selected from the group consisting of one or more α,β-ethylenically unsaturated non-acid monomers containing a $C_1$ to $C_9$ alkyl group, including linear and branched $C_1$ to $C_9$ alkyl esters of (meth)acrylic acid, vinyl esters of linear and branched $C_1$ to $C_{10}$ carboxylic acids and mixtures thereof.

10. A skin cleansing composition comprising:

(a) a low molecular weight, non-crosslinked, linear acrylic copolymer derived from at least one first monomeric component selected from the group consisting of (meth) acrylic acid and at least one second monomeric component selected from the group consisting of one or more $C_1$ to $C_9$ alkyl (meth)acrylates, wherein the low molecular weight copolymer has a number average molecular weight of about 100,000 or less; and (b) at least one non-ethoxylated anionic surfactant comprising more than about 2 weight percent of the skin care composition;

(c) wherein the total surfactant load of said skin cleansing composition is not greater than about 9 weight percent of the skin cleansing composition; the pH of said skin cleansing composition is about 6.2 or less; and the transmittance of said skin cleansing composition is greater than about 90%.

11. A skin cleansing composition comprising:

(a) a low molecular weight, non-crosslinked, linear acrylic copolymer derived from at least one first monomeric component selected from the group consisting of (meth) acrylic acid and at least one second monomeric component selected from the group consisting of one or more $C_1$ to $C_9$ alkyl (meth)acrylates, wherein the low molecular weight copolymer has a number average molecular weight of about 100,000 or less; and (b) at least one non-ethoxylated anionic surfactant comprising more than about 2 weight percent of the skin cleansing composition;

wherein the total surfactant load of said skin cleansing composition is not greater than about 7 weight percent of the skin cleansing composition; the pH of said skin cleansing composition is about 6.2 or less; and the skin cleansing composition has a count of 70 kcts/s or less in a light scattering test.

* * * * *